US011517523B2

(12) United States Patent
Montes et al.

(10) Patent No.: US 11,517,523 B2
(45) Date of Patent: *Dec. 6, 2022

(54) ORAL-SURFACE ADMINISTERED PREPARATION FOR THE PREVENTION OF ILLNESSES ACQUIRED VIA THE ORAL CAVITY AND THE PHARYNX

(71) Applicant: IntraMont Technologies, Inc., Hackensack, NJ (US)

(72) Inventors: Joseph G. Montes, Pensacola, FL (US); James Intrater, Hackensack, NJ (US)

(73) Assignee: INTRAMONT TECHNOLOGIES, INC., Hackensack, NJ (US)

( * ) Notice: Subject to any disclaimer, the term of this patent is extended or adjusted under 35 U.S.C. 154(b) by 119 days.

This patent is subject to a terminal disclaimer.

(21) Appl. No.: 16/353,802

(22) Filed: Mar. 14, 2019

(65) Prior Publication Data
US 2019/0209470 A1 Jul. 11, 2019

Related U.S. Application Data

(63) Continuation-in-part of application No. 15/701,465, filed on Sep. 12, 2017.

(51) Int. Cl.
| A61K 8/27 | (2006.01) |
| A61K 6/00 | (2020.01) |
| A61K 8/21 | (2006.01) |
| A61K 9/68 | (2006.01) |
| A61K 9/08 | (2006.01) |
| A61Q 11/00 | (2006.01) |
| A61K 9/00 | (2006.01) |
| A61K 33/16 | (2006.01) |
| A61K 31/555 | (2006.01) |
| A61K 47/46 | (2006.01) |
| A61K 31/315 | (2006.01) |
| A61K 8/60 | (2006.01) |
| A61K 31/05 | (2006.01) |
| A61K 33/30 | (2006.01) |

(52) U.S. Cl.
CPC ............ A61K 9/0053 (2013.01); A61K 8/602 (2013.01); A61K 9/0056 (2013.01); A61K 9/0063 (2013.01); A61K 31/05 (2013.01); A61K 31/315 (2013.01); A61K 31/555 (2013.01); A61K 33/16 (2013.01); A61K 33/30 (2013.01); A61K 47/46 (2013.01); A61Q 11/00 (2013.01); A61K 9/006 (2013.01); A61K 9/0058 (2013.01)

(58) Field of Classification Search
CPC .......... A61K 33/16; A61K 8/21; A61K 33/30; A61K 2800/92; A61K 6/69; A61K 31/315; A61K 2300/00; A61K 8/27; A61K 8/042; A61Q 11/00; A61P 31/16
See application file for complete search history.

(56) References Cited

U.S. PATENT DOCUMENTS

| 4,146,606 | A | 3/1979 | Yamaga et al. |
| 4,996,200 | A | 2/1991 | Nishimura et al. |
| 6,169,118 | B1 | 1/2001 | Bilali |
| 2002/0006386 | A1 | 1/2002 | Ibsen et al. |
| 2006/0134020 | A1* | 6/2006 | Robinson ............ A61K 8/21 424/52 |
| 2006/0194164 | A1 | 8/2006 | Altshuler et al. |
| 2007/0092552 | A1 | 4/2007 | Clarot |
| 2012/0207686 | A1* | 8/2012 | Fruge ............... A61P 31/04 424/52 |
| 2013/0272973 | A1 | 10/2013 | Boyd et al. |
| 2015/0182445 | A1 | 7/2015 | Ramirez |
| 2015/0224202 | A1 | 8/2015 | Stevenson et al. |
| 2017/0007643 | A1 | 1/2017 | Huang et al. |

(Continued)

FOREIGN PATENT DOCUMENTS

| CN | 102228479 A | * 11/2011 |
| EP | 2588067 | 5/2013 |

(Continued)

OTHER PUBLICATIONS

GW Kent. Laffort Tanin Galalcool 1 kg. Sep. 10, 2013. <https://web.archive.org/web/20130910021609/https://www.gwkent.com/laffort-tanin-galalcool-1-kg.html>. (Year: 2013).*
Davison, Nicola. Why can't we cure the common cold? Oct. 6, 2017. The Guardian. <https://www.theguardian.com/news/2017/oct/06/why-cant-we-cure-the-common-cold>. (Year: 2017).*
The Bottle Jar Store. Tanin Galalcool 1kg. Date retrieved: May 17, 2022. <https://www.thebottlejarstore.co.uk/product/tanin-galalcool-1kg/>. (Year: 2022).*
International Search Report and Written Opinion, dated Jun. 15, 2020, from corresponding International Application No. PCT/US20/22903.
Rao et al., "Zinc for the common cold—not if, but when", The Journal of Family Practice, Nov. 2011, 60(11): 669-671.

(Continued)

Primary Examiner — Tracy Liu
(74) Attorney, Agent, or Firm — Pearl Cohen Zedek Latzer Baratz LLP

(57) ABSTRACT

The invention includes a toothpaste or other orally applied product to be used at least once daily to help prevent or inhibit the acquisition of a number of infections by oral or pharyngeal tissues, particularly including the "common" cold. These compositions possess a combination of ingredients that is not found in other toothpastes or other orally applied products, and these ingredients work together to synergistically interfere with the acquisition of a number of pathogens. The toothpastes will have the usual dentifrice ingredients known to prevent tooth decay, as well as those that reduce halitosis (i.e., bad breath), and prevent gingivitis. In addition, the toothpastes will include one or more of: 1) GALALCOOL® as an individual compound, and not as an extract component; 2) zinc protoporphyrin IX; and 3) one or more other colorless or low-color tannin(s) each as an individual compound, and not as an extract component.

5 Claims, No Drawings

(56) References Cited

U.S. PATENT DOCUMENTS

2019/0209470 A1 7/2019 Montes et al.

FOREIGN PATENT DOCUMENTS

| WO | WO 2016/067283 | 5/2016 |
| WO | WO 2016/106072 | 6/2016 |

OTHER PUBLICATIONS

Wikipedia, "Tannic acid", Feb. 2, 2019, 8 pages (Retrieved May 26, 2020) Retrieved from Internet URL: https://en.wikipedia.org/wiki/Tannic_acid.

Jia et al., "A potential anti-tumor herbal medicine, Corilagin, inhibits ovarian cancer cell growth through blocking the TGF-β signaling pathways", BMC Complementary and Alternative Medicine (2013) 13:33, 11 pages.

Cushnie et al., "Antimicrobial activity of flavonoids", International Journal of Antimicrobial Agents, 26, 2005, pp. 343-356.

Buzzini et al., "Antimicrobial and Antiviral Activity of Hydrolysable Tannins", Mini-Reviews in Medicinal Chemistry, 2008, vol. 8, No. 12, pp. 1179-1187.

Sanz et al., "Antiplaque and Antigingivitis Toothpastes", Monograph Oral Sci. Basel, Karger, 2013, vol. 23, pp. 27-44.

Karamac, "Chelation of Cu(II), Zn(II), and Fe(II) by Tannin Constituents of Selected Edible Nuts", Int. J. Mol. Sci. 2009, 10, 5485-5497.

Guo et al., "Effect of Corilagin on anti-inflammation in HSV-1 encephalitis and HSV-1 infected microglias", European Journal of Pharmacology, 635 (2010) 79-86.

Cruz et al., "Heavy Metal Binding by Tannic Acid: A Voltammetric Study", Electroanalysis (12), 14, (2000): 1130-1137.

Gupta et al., "Phytochemistry and pharmacological activities of Haritaki—A review", Journal of Pharmacy Research 2010, 3(2), 417-424.

Labbe et al., "Zinc Protoporphyrin: A Metabolite with a Mission", Clinical Chemistry, 45:12, 2060-2072 (1999).

WebMD, Cold, Flu & Cough Health Center, "Zinc for Colds: Lozenges & Nasal Sprays", available at www.webmd.com/cold-and-flu/cold-guide/zinc-lozenges-cold-remedy.

Suara et al., "Effect of Zinc Salts on Respiratory Syncytial Virus Replication", Antimicrobial Agents and Chemotherapy, 48(3), Mar. 2004, 16 pages, available at www.ncbi.nlm.nih.gov/pmc/articles/PMC353050.

Huang et al., "Immobilization of plant polyphenol stabilized-Sn nanoparticles onto carbon nanotubes and their application in rechargeable lithium ion batteries", RSC Advances, 2013, 3, 5310-5313.

Yu et al., "Innovative use of silvichemical biomass and its derivatives for heavy metal sorption from wastewater", International Journal of Environment and Pollution, vol. 34, Nos. 1/2/3/4, 2008, pp. 427-450.

National Institutes of Health Office of Dietary Supplements, Zinc Fact Sheet for Health Professionals, 16 pages, available at https://ods.od.nih.gov/factsheets/Zinc-HealthProfessional.

Potduang et al., "The Development of Phyllanthus emblica and Zanthoxylum limonella Toothpaste", The 6$^{th}$ International Conference on Natural Products for Health and Beauty (NATPRO6), Jan. 21-23, 2016.

International Search Report and Written Opinion, dated Nov. 14, 2018, from corresponding International Application No. PCT/US18/49985.

Khare, "Indian Medicinal Plants: An Illustrated Dictionary," Springer, Berlin, Germany, p. 532 (2007).

Basri et al., "In Vitro Antibacterial Activity of Galls of Quercus infectoria Olivier against Oral Pathogens", Evidence-Based Complementary and Alternative Medicine, vol. 2012, Article ID 632796, 6 pages (2012).

Laffort, "TANNIN GALACOOL®", Product Data Sheet, 2 pages (2017).

Chowdury et al., "Herbal Toothpaste—A possible remedy for oral cancer", Journal of Natural Products, vol. 6, pp. 44-55 (2013).

Liu et al., "Gelatinization of cornstarch with different amylose/amylopectin content", Carbohydrate Polymers, 65(3):357-363 (2006).

Das et al., "Role of phytoconstituents in the management of COVID-19", Chemico-Biological Interactions, Mar. 30, 2021, 341:109449; 27 pages; https://doi.org/10.1016/j.cbi.2021.109449.

Du et al., "Discovery of chebulagic acid and punicalagin as novel allosteric inhibitors of SARS-CoV-2 3CL$^{pro}$", Antiviral Research, Apr. 17, 2021, 190:105075, 8 pages; https://doi.org/10.1016/j.antiviral.2021.105075.

Falade et al., "In silico investigation of saponins and tannins as potential inhibitors of SARS-CoV-2 main protease (M$^{pro}$)", In Silico Pharmacology, Jan. 6, 2021, 9:9, 15 pages; https://doi.org/10.1007/s40203-020-00071-w.

Goli, "Review of novel human β-coronavirus (2019-nCoV or SARSCoV-2) from the food industry perspective—Appropriate approaches to food production technology", Food Science & Nutrition, Aug. 30, 2020; 8:5228-5237; DOI: 10.1002/fsn3.1892.

Houston et al., "Potentiated virucidal activity of pomegranate rind extract (PRE) and punicalagin against Herpes simplex virus (HSV) when co-administered with zinc (II) ions, and antiviral activity of PRE against HSV and acyclovir-resistant HSV", PLoS One, Jun. 30, 2017, 12(6): e0179291, 15 pages; https://doi.org/10.1371/journal.pone.0179291.

Khalifa et al., "Tannins inhibit SARS-CoV-2 through binding with catalytic dyad residues of 3CL$^{pro}$: An in silico approach with 19 structural different hydrolysable tannins", Journal of Food Biochemistry, Jul. 21, 2020, 00:e13432, 19 pages; DOI: 10.1111/jfbc.13432.

Kouhpayeh et al., "The Molecular Basis of COVID-19 Pathogenesis, Conventional and Nanomedicine Therapy", International Journal of Molecular Sciences, May 21, 2021, 22, 5438, 28 pages; https://doi.org/10.3390/ijms22115438.

Liu et al., "Identification of hydrolyzable tannins (punicalagin, punicalin and geraniin) as novel inhibitors of hepatitis B virus covalently closed circular DNA", Antiviral Research, Oct. 2016, 134:97-107; doi:10.1016/j.antiviral.2016.08.026.

Loaiza-Cano et al., "Antiviral Role of Phenolic Compounds against Dengue Virus: A Review", Biomolecules, 2021, 11, 11, 28 pages, https://dx.doi.org/10.3390/biom11010011.

Mehany et al., "Polyphenols as promising biologically active substances for preventing SARS-CoV-2: A review with research evidence and underlying mechanisms", Food Bioscience, Jan. 20, 2021, 40:100891, 12 pages, https://doi.org/10.1016/j.fbio.2021.100891.

Molino et al., "Natural tannin extracts supplementation for COVID-19 patients (TanCOVID): a structured summary of a study protocol for a randomized controlled trial", Trials, Apr. 28, 2021, 22:310, 3 pages, https://doi.org/10.1186/s13063-021-05281-x.

Orlowski et al., "Antiviral Activity of Tannic Acid Modified Silver Nanoparticles: Potential to Activate Immune Response in Herpes Genitalis", Viruses, Sep. 26, 2018, 10, 524, 15 pages; doi:10.3390/v10100524.

Pong et al., "Anti-dengue virus serotype 2 activity of tannins from porcupine dates", Chinese Medicine, (2020) 15:49, 14 pages; https://doi.org/10.1186/s13020-020-00329-7.

Pooja et al., "Unravelling high-affinity binding compounds towards transmembrane Protease serine 2 enzyme in treating SARS-CoV-2 infection using molecular Modelling and docking studies", European Journal of Pharmacology, Oct. 29, 2020, 890:173688, 13 pages; https://doi.org/10.1016/j.ejphar.2020.173688.

Saadh et al., "Punicalagin and zinc (II) ions inhibit the activity of SARS-CoV-2 3CL-protease in vitro", European Review for Medical and Pharmacological Sciences, 2021; 25: 3908-3913.

Siqueira et al., "Antiviral Potential of Spondias mombin L. Leaves Extract Against Herpes Simplex Virus Type-1 Replication Using In Vitro and In Silico Approaches", Planta Med., Apr. 2020; 86:505-515; DOI https://doi.org/10.1055/a-1135-9066.

Ueda et al., "Inactivation of Pathogenic Viruses by Plant-Derived Tannins: Strong Effects of Extracts from Persimmon (Diospyros kaki) on a Broad Range of Viruses", PLoS One, Jan. 2013, 8(1): e55343, 10 pages.

(56) References Cited

OTHER PUBLICATIONS

Wang et al., "A single-molecule atomic force microscopy study reveals the antiviral mechanism of tannin and its derivatives", Nanoscale, Aug. 2019, 11:16368-16376; DOI: 10.1039/c9nr05410c.

Wang et al., "A single-molecule atomic force microscopy study reveals the antiviral mechanism of tannin and its derivatives", Electronic Supplementary Material (ESI) for Nanoscale, The Royal Society of Chemistry 2019, 8 pages.

Yang et al., "Corilagin prevents SARS-CoV-2 infection by targeting RBD-ACE2 binding", Phytomedicine, May 5, 2021, 87:153591, 12 pages; https://doi.org/10.1016/j.phymed.2021.153591.

Yousaf et al., "Phytochemical profiling and antiviral activity of Ajuga bracteosa, Ajuga parviflora, Berberis lycium and Citrus lemon against Hepatitis C Virus", Microbial Pathogenesis, Mar. 2018, 118:154-158; https://doi.org/10.1016/j.micpath.2018.03.030.

Extended European Search Report, dated May 18, 2021, from corresponding European Patent Application No. 18855931.4.

Database GNPD (Online) MINTEL, Jan. 4, 2012, Anonymous: "Homeopathic Cold Relief Lozenges", XP055800390, Database accession No. 1696232.

Database GNPD (Online) MINTEL, Mar. 17, 2017, Anonymous: "Thera Zinc Spray", XP055800381, Database accession No. 4688265.

Houston et al., "In vitro permeation and biological activity of punicalagin and zinc (II) across skin and mucous membranes prone to Herpes simplex virus infection", European Journal of Pharmaceutical Sciences, Aug. 2016, vol. 96, pp. 99-106.

Database GNPD (Online) MINTEL, Mar. 8, 2011, Anonymous: "Natural Toothpaste", XP055800376, Database accession No. 1514684.

\* cited by examiner

ORAL-SURFACE ADMINISTERED PREPARATION FOR THE PREVENTION OF ILLNESSES ACQUIRED VIA THE ORAL CAVITY AND THE PHARYNX

CROSS-REFERENCE TO RELATED APPLICATIONS

This application is a continuation-in-part of U.S. patent application Ser. No. 15/701,465, filed Sep. 12, 2017, which is hereby incorporated by reference.

FIELD OF THE INVENTION

The invention relates to compositions and formulations for preventing or inhibiting the acquisition of infections via the oral cavity and pharynx, as well as methods of using and making these compositions and formulations. Specifically, the invention relates to toothpastes, in the form of a paste or gel; or mouthwashes or oral rinses; or chewable materials, such as a chewing gum or other orally administered preparation for the prevention or inhibition of colds or other upper respiratory and pharyngeal infections, as well as to their use to administering these compositions and formulations to the mouth and/or pharynx to prevent or inhibit colds and/or other upper respiratory and pharyngeal infections.

BACKGROUND OF THE INVENTION

A number of toothpastes and mouthwashes already on the market are known to fight tooth decay (usually through fluoride), to reduce the incidence of gingivitis (usually by the action of triclosan and/or of a zinc salt, such as zinc acetate, zinc gluconate, zinc lactate, or zinc chloride (M. Sanz, et al., Antiplaque and Antigingivitis toothpastes. *Monograph Oral Sci* (2013) 23:27-44)), to help clean out the mouth of food particles, and to produce "fresh breath". Thus, while currently available over-the-counter toothpastes address the need for the prevention of dental caries (bacteria-induced tooth decay leading to cavities), gingivitis, amelioration of sensitive teeth, and oral hygiene in general, there is a need in the art for toothpastes and other orally administered preparations that includes ingredients that will enhance the ability of the toothpaste or preparation to prevent or inhibit the acquisition of or reduce the incidence or likelihood of a number of conditions, including the common cold and a host of other pathological conditions caused by pathogenic viruses, bacteria, and fungi, or possibly other conditions (e.g., canker sores, ear infections, etc.). Thus, there is a need in the art for toothpastes and mouthwashes and other formulations that will prevent or inhibit the acquisition of or reduce the incidence or likelihood of a number of infections via the oral cavity and the pharynx, while at the same time function as most toothpastes and mouthwashes in preventing cavities and cleansing the oral cavity.

SUMMARY OF THE INVENTION

Described here are formulations that when applied to the mouth in the form of one of its embodiments will help prevent or inhibit the acquisition of a large number of possible pathogenic conditions that originate from interaction between a pathogen, such as a virus, bacterium, or fungus, and tissues present in the mouth and/or pharynx. In the preferred embodiment of a toothpaste or gel it can be delivered adequately into the oral and pharyngeal surfaces. By the customary-at least daily-brushing of the teeth, followed by minimal rinsing or merely spitting out of the preparation, typically a toothpaste, the user will be protected from acquiring or have a lower incidence of a number of pathogenic conditions, especially the common cold. Suitable ingredients known in the art will form the base of embodiments of the invention, to which will be added the ingredients of a dissolved zinc salt, and one or more astringent compounds selected from GALALCOOL®, another colorless or low-color tannin, and zinc protoporphyrin IX.

In one aspect, provided herein are compositions formulated as a toothpaste or other orally administered preparation for the prevention or inhibition of colds or other upper respiratory and pharyngeal infections, comprising a dentifrice gel or paste comprising a colorless or low-color tannin (including GALALCOOL®, a low-color tannin extracted from chestnut or oak gallnuts for addition to white wine, sold by Laffort Company based in France), or another mass-produced, colorless or low-color or white-colored tannin, or a combination of GALALCOOL® and one or more other mass-produced, colorless or low-color tannin. In some embodiments, the toothpaste or other orally administered preparation further comprises zinc protoporphyrin IX. In some embodiments, the toothpaste or other orally administered preparation further comprises a free zinc salt.

In another aspect, provided herein are compositions formulated as chewing gum, oral rinse, mouth wash, or aerosol for the prevention or inhibition of colds or other upper respiratory and pharyngeal infections, comprising a solvent or other vehicle comprising GALALCOOL®, or another mass-produced, colorless or low-color or white-colored tannin, or a combination of GALALCOOL® and one or more other mass-produced, colorless or low-color tannin. In some embodiments, the chewing gum, oral rinse, mouth wash, or aerosol further comprises zinc protoporphyrin IX. In some embodiments, the chewing gum, oral rinse, mouth wash, or aerosol further comprises a free zinc salt.

In another aspect, provided herein, are methods of preventing or inhibiting the acquisition of or reduce the incidence or likelihood of a cold or other upper respiratory or pharyngeal infection by administering a composition or formulation described herein to the mouth and/or pharynx of a subject. In yet another aspect, provided herein, are methods of making a composition or formulation described herein.

Other features and advantages of the present invention will become apparent from the following detailed description examples. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In some embodiments, described herein, is a toothpaste, in the form of a paste or gel; or a mouthwash or oral rinse; or a chewable material, such as a chewing gum; or other orally administered preparation that will contain a base preparation with suitable ingredients known in the art, such as a fluoride, a detergent (such as sodium lauryl sulfate), a solvent (such as glycerol and/or propylene glycol), a salt of zinc, an abrasive (such as fumed silica), an antibacterial (such as triclosan), a flavoring agent, including a sweetener, and any other suitable ingredient deemed useful or necessary for the composition or formulation. Added to the base preparation or formulation will be one or more of the following:

(1) an astringent compound, a tannin called GALALCOOL®;

(2) an astringent compound, a porphyrin, called zinc protoporphyrin IX; and (3) an astringent compound, a colorless or low-color tannin other than GALALCOOL® (e.g., TANFRESH® from the same company as GALALCOOL®)

The above ingredients will produce their effects on preventing or inhibiting the acquisition of a number of pathogens, including viruses that cause colds, such as rhinovirus, including a number of oral bacteria that may be pathogenic, for example, those that may result in gingivitis, and including oral fungi that may produce thrush. Typically, the user when employing a toothbrush to apply a toothpaste described herein will brush with the toothpaste at least once a day, and immediately following brushing will either non-vigorously spit out the preparation only once and/or rinse it out with water.

The toothpaste or other embodiment of the invention will prevent or inhibit the acquisition of or reduce the incidence or likelihood of a number of infections via the oral cavity and the pharynx, while at the same time function as most toothpastes and mouthwashes in preventing cavities and cleansing the oral cavity.

One of the present inventors was commonly beset with the common cold most of his life, typically acquiring 3 to 4 colds per year. However, beginning about twelve years ago he started to correlate lower incidence of his own colds to select ingredients a person might place deliberately in his mouth. Some have been advanced a probable scientific basis, while others have been anecdotally linked to lower incidence of disease, including 1. Salts of zinc;
2. Stannous fluoride or other fluoride;
3. Sodium lauryl sulfate; and
4. Polyphenols, such as tannins.

A number of toothpastes and mouthwashes already on the market are known to fight tooth decay (usually through fluoride), to reduce the incidence of gingivitis (usually by the action of triclosan and/or of a zinc salt, such as zinc acetate, zinc gluconate, zinc lactate, or zinc chloride (M. Sanz, et al., Antiplaque and Antigingivitis toothpastes. *Monograph Oral Sci* (2013) 23:27-44)), to help clean out the mouth of food particles, and to produce "fresh breath." However, no toothpaste or mouthwash has the unique combination of ingredients in embodiments of the present invention; in particular, an ingredient in the latter toothpaste provides for the slower release of zinc salts. Zinc salts have been used for many years in a number of toothpastes to prevent gingivitis, but given that zinc salts can also be used to reduce the symptoms of the common cold by apparently reducing the infectivity of the cold virus to mucous membranes, it makes sense to provide for a steadier source of zinc ions by using a method, described below, for rendering zinc salts present in the oral cavity for a longer time period than normally achieved by brushing with current toothpastes. The new toothpaste is typically used at least once per day through brushing with a toothbrush; nonetheless, it can also be used two or more times per day without ill effects or reduction in efficacy. After brushing, the user is to spit out the ingredients from his mouth by no more than one rinse with water, or even without partially or fully rinsing, in order to allow for the adequate retention of residues of the toothpaste.

With regards to the zinc salts, it is now known that zinc ions can prevent the attachment of rhinovirus to cells, and that zinc-containing lozenges can mitigate the symptoms and duration of the common cold (See WedMD. Cold, Flu & Cough Health Center-Zinc for Colds: Lozenges & Nasal Sprays. Available at www.webmd.com/cold-and-flu/cold-guide/zinc-lozenges-cold-remedy; and National Institutes of Health Office of Dietary Supplements. Zinc Fact Sheet for Health Professionals. Available at ods.od.nih.gov/factsheets/Zinc-HealthProfessional). However, the observation that one-and-a-half days of not exposing himself to such ingredients resulted in again the acquiring a common cold by one of the inventors, suggested that extension of the residing time of the anti-colds ingredients in the mouth and pharynx could enhance the effectiveness of cold prevention by zinc compounds. Thus, one of the inventors came up with a method for accomplishing the latter goal of the toothpaste. It should be noted that zinc seems to have effects on other common viruses, such as respiratory syncytial virus (Effect of Zinc Salts on Respiratory Syncytial Virus Replication—NCBI. Available at www.ncbi.nlm.nih.gov/pmc/articles/PMC353050), and thus extending the residing time of zinc salts could produce other health benefits of the toothpaste.

There may be a host of infectious viruses whose ability to infect individuals can be hampered by a toothpaste that contains zinc and applies the latter to the oral cavity, gums, and pharynx. In addition, zinc salts are known to have anti-bacterial and anti-fungal properties as well, that along with fluoride salts, detergents, and other components will also help reduce the frequency of acquiring fungal and bacterial infections. Thus, embodiments of the invention address a broad spectrum of pathologies acquired local to the oral cavity and the pharynx.

A property of zinc salts that correlates with their ability to prevent acquisition of colds (rhinoviruses and other viruses) is that of astringency (see www.britannica.com/science/astringent. Accessed Sep. 14, 2016). Zinc belongs in the class of astringents called "metallic astringents", namely those that cause coagulation effects on the surface layers of cells. This would suggest that coagulation of proteins is involved in prevention or inhibition of acquisition of colds. Given that protein coats called capsids surround all viruses, coagulation of the proteins in the coats would radically interfere with the attachment of the virions (individual virus particles) to their cell hosts; this would apply specifically to the host cells superficially exposed to astringents at their surfaces. However, many viruses also have an "envelope" of lipid surrounding the protein coat, so that coagulation effects of an astringent may be interfered with; furthermore, such an envelope is believed to interfere with immune defenses by interfering with protein (virus)-to-protein (antibody) binding. However, toothpastes and other oral and pharyngeal preparations contain surfactants of high efficiency, such as sodium lauryl sulfate, thus helping to solubilize the lipid envelopes of the viruses and thus resulting in the exposure of the protein capsid to the astringent in the preparation. Thus, it appears that a detergent environment is a co-factor in the successful prevention by an astringent (including a zinc salt) of the acquisition of an infection from an enveloped virus. As most colds are caused by rhinoviruses, and they are not enveloped viruses, the need for a detergent co-factor to prevent acquiring them in the pharynx is probably not significant. Nonetheless, embodiments of the invention are intended for the prevention or inhibition of acquisition of not just cold viruses, but also other viruses acquired in the mouth or pharynx, and many of them are enveloped viruses. Among enveloped viruses that embodiments of the invention may prevent or inhibit are the following: herpes simplex I (oral herpes); varicella virus (chicken pox); influenza virus; flavivirus (hepatitis C); respiratory syncytial virus, among others (medimoon.com/2014/03/list-of-some-common-viral-diseases-and-their-treatment). It should be noted that the point of initial acquisition of virus is not necessarily representative of the virus's final distribution and symptomatology. For example, one may acquire hepatitis C through the pharynx, but the primary focus of the disease is the liver. By the same token, an inner ear infection (otitis media) can be secondarily acquired from a viral or bacterial infection acquired first in the pharynx.

Thus, the property of astringency is linked to stopping the acquisition of viruses by cells of mucous membranes. In embodiments of the present invention, an isolated tannin called GALALCOOL® is an ingredient that will be used to prevent the acquisition of pathological conditions caused by microbes, including viruses and bacteria, via the oral cavity and pharynx. This is at least in part because of its known astringent properties. It will act as a coagulation agent as in the case of zinc. However, unlike zinc alone, it will have an affinity for mucus secretions not expected with the ionic form of zinc (from zinc salts). Thus, it may be able to adhere for longer times to certain mouth and pharyngeal surfaces. Furthermore, it has a beneficial anti-inflammatory property as indicated in at least one study (P. Buzzini, et al., Antimicrobial and Antiviral Activity of Hydrolysable Tannins. *Mini-Reviews in Medicinal Chemistry* (2008) 8:1179-1187; Yuan-Jin Guo et al., Effect of Corilagin on Anti-inflammation in HSV-1 Encephalitis and HSV-1 Infected Microglias. *European Journal of Pharmacology* (2010) 635:79-86; J. Luoqi, et al., A Potential Anti-tumor Herbal Medicine, Corilagin, Inhibits Ovarian Cancer Cell Growth Through Blocking the TGF-β Signaling Pathways. *BMC Complementary and Alternative Medicine* (2013) 13:33; N. Bismelah, et al., *Journal of Medicinal Plants Studies* (2016) 4:18-23; A Gupta, et al., Phytochemistry and Pharmacological Activities of Haritaki—A Review. *Journal of Pharmacy Research* (2010) 3:417-424). While an extract of the Indian gooseberry has been proposed as a toothpaste ingredient (P Potduang, et al., The Development of *Phyllanthus emblica and Zanthoxylum limonella* Toothpaste. The 6th International Conference on Natural Products for Health and Beauty (NATPRO6), Jan. 21-23, 2016), and that extract has a tannin, corilagin as one of its constituents, many other constituents exist in that extract. Furthermore, in that case, corilagin was not singled out as the active ingredient in the preparation nor was its mode of action as an antimicrobial and anti-inflammatory revealed. It should be noted also that the preferred concentration of GALALCOOL® or other low-color or colorless tannin to be used in embodiments of the present invention is 0.03% by weight, which is much lower than the extract concentration maximum of 0.2% by weight in the toothpaste with the extract proposed by P. Potduang, et al. However, a much higher concentration of a tannin may prove optimal in the future, and as per claims of this patent, it may be as high as 10% of the toothpaste composition by weight, which is very much higher than 0.2%. In such a case, the concentration of pure tannin in embodiments of the present invention will exceed that in the Indian gooseberry toothpaste by many factors.

Other astringent compounds, namely tannins that are colorless or of low color, would be alternative ingredients to GALALCOOL®, although one or more such tannins may also be used together with the latter to extend efficacy of the dentifrice. Tannins, polyphenolic compounds of which GALALCOOL® is only one example, are found at relatively high concentration in many edible plants. They are astringent and thus typically result in the precipitation of proteins, and furthermore, given that most viruses have a protein capsid (shell) interfacing with the external environment, this could be of central importance in removing viruses from free distribution in the mouth and throat (A Manual of Materia Medica and Pharmacology, p. 282. DMR Culbreck. Lea and Febiger, Philadelphia, 1927). In addition, this would suggest an ability, like that of zinc, to interfere with the attachment of certain viruses to cells of mucous membranes, while its very low water solubility suggests that it may preferentially sequester at different locations in the mouth, specifically those not easily wetted, unlike zinc salts. Also, it has been reported that polyphenols (such as the flavonoid compound quercetin) have antibacterial properties, hence possessing other potential benefits to oral health, and not just as a potential anti-viral agent (T P T Cushnie and A J Lamb, Antimicrobial Activity of Flavonoids. *International Journal of Antimicrobial Agents* (2005) 26:343). Other tannins beside GALALCOOL® will be considered as active ingredients in certain embodiments of the invention. However, as tannins typically are dark-colored compounds, only certain tannins will be considered as potential co-ingredients in certain embodiments of the invention; tannins typically stain tooth enamel, so it is important that only colorless or low-color tannins be used in certain embodiments of the invention. They may also stain toothbrush bristles, producing another psychologically objectionable result. GALALCOOL® and/or other tannin(s) or polyphenolic astringent compounds (e.g., TANFRESH®) used in embodiments of the invention will be compound(s) displaying potentially synergistic efficacy with the other component ingredients of embodiments of the invention. As for concerns on the toxicology of tannins, the Select Committee on GRAS substances has weighed in on the potential toxicity of tannic acid (as a hydrolysable gallotannin prototype) as follows (from https://www.fda.gov/Food/IngredientsPackagingLabeling/GRAS/SCOGS/ucm261485.htm, accessed Aug. 23, 2017): "The ingredients in the compositions of embodiments of the invention are at concentrations known not to be toxic, even if the product is inadvertently completely swallowed every time it is used. The Select Committee, therefore, in the light of the foregoing concludes that:

"There is no evidence in the available information on tannic acid (hydrolyzable gallotannins) that demonstrates or suggests reasonable grounds to suspect a hazard to the public when it is used at levels that are now current and in the manner now practiced. However, it is not possible to determine, without additional data, whether a significant increase in consumption would constitute a dietary hazard."

Finally, another ingredient, zinc protoporphyrin IX (R F Labbe, et al., Zinc Protoporphyrin: A Metabolite with a Mission. *Clinical Chemistry* (1999) 45:2060-2072), may be a constituent of the orally administered product. In addition to being yet another zinc source, in this case of longer persistence, and an astringent in its own right, it is a known carrier of divalent ions (such as zinc ion), thus creating a more persistent zinc source that assists in conveying zinc to more extensive areas of the mouth and pharynx, and itself prolonging astringency in the latter areas. Zinc salts, being water soluble, will more easily wash out of the mouth and areas continuous with and beyond the oral cavity.

Because each ingredient has different physical and chemical properties, however, notwithstanding their commonality of astringency, a synergistic effect will result because of their differences in structural stability, affinities for each other, affinities for different surfaces in the mouth and pharynx, and tendencies to associate and adhere to different secretions.

Although currently available over-the-counter toothpastes address the need for the prevention of dental caries (bacteria-induced tooth decay leading to cavities), gingivitis, amelioration of sensitive teeth, and oral hygiene in general, the novel toothpastes described here may work in a synergistic mode by combining multiple ingredients. It can be expected that since the surface affinity of each ingredient differs according to specific tissue (e.g., gums vs. mucous membranes of the pharynx vs. tooth enamel), that the different ingredients will work to create a more thorough exposure of different tissues to the effective ingredients; furthermore, different strains of bacteria and viruses may differ substantially in susceptibility to the different ingredients, so that diversity in the ingredients should have more effect than their use at simply the highest safe concentration of each single ingredient known to be effective. The ingredients in the novel toothpaste will be present in a unique combination that includes ingredients that will enhance the ability of the toothpaste to prevent the acquisition of a number of conditions, including the common cold and a host of other pathological conditions caused by pathogenic viruses, bacteria, and fungi, or possibly other conditions (e.g., canker sores, ear infections, etc.). The consumer of the toothpaste should preferably need only brush his teeth once per day to attain desired results.

The following examples are presented in order to more fully illustrate the preferred embodiments of the invention. They should in no way be construed, however, as limiting the broad scope of the invention.

Embodiments of the invention include:

1. A composition formulated as a toothpaste or other orally administered preparation for the prevention or inhibition of colds or other upper respiratory and pharyngeal infections, comprising a dentifrice gel or paste comprising GALALCOOL®, one or more other colorless or low-color tannin(s), or a combination of GALALCOOL® and one or more other colorless or low-color tannin(s).

2. The composition of embodiment 1, further comprising a free zinc salt.

3. The composition of embodiment 2, wherein the zinc salt is an organic zinc salt.

4. The composition of embodiment 3, wherein the organic zinc salt is selected from the group consisting of zinc gluconate, zinc lactate, zinc acetate, and combinations thereof.

5. The composition of embodiment 4, wherein the organic zinc salt is zinc gluconate.

6. The composition of embodiment 2, wherein the zinc salt is an inorganic zinc salt.

7. The composition of embodiment 6, wherein the inorganic zinc salt is selected from the group consisting of zinc chloride, zinc sulphate, zinc carbonate, and combinations thereof.

8. The composition of any one of embodiments 1 to 7, wherein the GALALCOOL® is 0.01% to 10% by weight of the composition.

9. The composition of embodiment 8, wherein the GALALCOOL® is 0.03% by weight of the composition.

10. The composition of any one of embodiments 1 to 9, wherein another colorless or low-color tannin, or each other colorless or low-color tannin, is 0.01% to 10% by weight of the composition.

11. The composition of embodiment 10, wherein the one or more other colorless or low-color tannin(s) is each 0.03% by weight of the composition.

12. The composition of embodiments 10 or 11, wherein the concentration of GALALCOOL® is zero.

13. The composition of any one of embodiments 1 to 11, wherein the composition comprises a combination of GALALCOOL® and one or more other colorless or low-color tannin(s).

14. The composition of embodiment 13, wherein the GALALCOOL® is 0.01% to 10% by weight and that of another or each other colorless or low-color tannin is 0.01% to 10% by weight of the composition, respectively.

15. The composition of embodiment 13, wherein the GALALCOOL® is 0.03% by weight and that of another or each other colorless or low-color tannin is 0.03% by weight of the composition, respectively.

16. The composition of any one of embodiments 1 to 15, further comprising zinc protoporphyrin IX.

17. The composition of embodiment 16, wherein the zinc protoporphyrin IX ranges from 0.1% to 5% by weight of the composition.

18. The composition of embodiment 17, wherein the zinc protoporphyrin IX is 0.5% by weight of the composition.

19. The composition of any one of embodiments 2 to 18, wherein the free zinc salt ranges from 0.1% to 0.5% by weight of the composition.

20. The composition of embodiment 19, wherein the free zinc salt is 0.4% by weight of the composition.

21. The composition of any one of embodiments 1 to 20, further comprising a fluoride compound.

22. A composition formulated as chewing gum, oral rinse, mouth wash, or aerosol for the prevention or inhibition of colds or other upper respiratory and pharyngeal infections, comprising a solvent or other vehicle comprising GALALCOOL®, one or more other colorless or low-color tannin(s), or a combination of GALALCOOL® and one or more other colorless or low-color tannin(s).

23. The composition of embodiment 22, further comprising a free zinc salt.

24. The composition of embodiment 23, wherein the zinc salt is an organic zinc salt.

25. The composition of embodiment 24, wherein the organic zinc salt is selected from the group consisting of zinc gluconate, zinc lactate, zinc acetate, and combinations thereof.

26. The composition of embodiment 24, wherein the organic zinc salt is zinc gluconate.

27. The composition of embodiment 23, wherein the zinc salt is an inorganic zinc salt.

28. The composition of embodiment 27, wherein the inorganic zinc salt is selected from the group consisting of zinc chloride, zinc sulphate, zinc carbonate, and combinations thereof.

29. The composition of any one of embodiments 22 to 28, wherein the GALALCOOL® is 0.01% to 10% by weight of the composition.

30. The composition of embodiment 29, wherein the GALALCOOL® is 0.03% by weight of the composition.

31. The composition of any one of embodiments 22 to 30, wherein the concentration of one or more other colorless or low-color tannin(s) is each 0.01% to 10% by weight of the composition.

32. The composition of embodiment 31, wherein one or more other colorless or low-color tannin(s) is each 0.01% by weight of the composition.

33. The composition of any one of embodiments 22 to 32, wherein the composition comprises a combination of GALALCOOL® and one or more other colorless or low-color tannin(s).

34. The composition of embodiment 33, wherein the GALALCOOL® is 0.01% to 10% by weight and that of one or more other colorless or low-color tannin(s) is each 0.01% to 10% by weight of the composition, respectively.

35. The composition of embodiment 34, wherein the GALALCOOL® is 0.03% by weight and that of one or more other colorless or low-color tannin(s) is each 0.03% by weight of the composition, respectively.

36. The composition of any one of embodiments 22 to 35, further comprising zinc protoporphyrin IX.

37. The composition of embodiment 36, wherein the zinc protoporphyrin IX ranges from 0.1% to 5% by weight of the composition.

38. The composition of embodiment 37, wherein the zinc protoporphyrin IX is 0.5% by weight of the composition.

39. The composition of any one of embodiments 23 to 38, wherein the free zinc salt ranges from 0.1% to 0.5% by weight of the composition.

40. The composition of embodiment 39, wherein the free zinc salt is 0.4% by weight of the composition.

41. The composition of any one of embodiments 22 to 40, further comprising a fluoride compound. 42. The composition of any one of embodiments 1 to 21, further comprising a malleable or squeezable tube in which the composition is stored.

43. The composition of any one of embodiments 1 to 21 or 42, wherein the composition is formulated as a toothpaste and as a translucent gel or as a paste.

44. A method of preventing or inhibiting the acquisition of a cold or other upper respiratory or pharyngeal infection comprising administering to a subject the toothpaste of any one of embodiments 1 to 21 or 42 to 43.

45. A method of reducing the incidence or likelihood of a cold or other upper respiratory or pharyngeal infection comprising administering to a subject the toothpaste of any one of embodiments 1 to 21 or 42 to 43.

46. The method of embodiments 44 or 45, wherein the step of administering comprises brushing of the subject's teeth.

47. The composition of any one of embodiments 22 to 41, wherein the composition is formulated as an oral rinse or mouthwash.

48. A method of preventing or inhibiting the acquisition of a cold or other upper respiratory or pharyngeal infection comprising administering to a subject the oral rinse or mouthwash of embodiment 47.

49. A method of reducing the incidence or likelihood of a cold or other upper respiratory or pharyngeal infection comprising administering to a subject the oral rinse or mouthwash of embodiment 47.

50. The method of embodiments 48 or 49, wherein the step of administering comprises rinsing out the subject's mouth with the oral rinse or mouthwash.

51. The composition of any one of embodiments 22 to 41, wherein the composition is formulated as a chewing gum.

52. A method of preventing or inhibiting the acquisition of a cold or other upper respiratory or pharyngeal infection comprising administering to a subject the chewing gum of embodiment 51.

53. A method of reducing the incidence or likelihood of a cold or other upper respiratory or pharyngeal infection comprising administering to a subject the chewing gum of embodiment 51.

54. The method of embodiments 52 or 53, wherein the step of administering comprises chewing the chewing gum.

55. The composition of any one of embodiments 22 to 41, wherein the composition is formulated as an aerosol to be sprayed into the mouth and/or pharynx.

56. A method of preventing or inhibiting the acquisition of a cold or other upper respiratory or pharyngeal infection comprising administering to a subject the aerosol of embodiment 55.

57. A method of reducing the incidence or likelihood of a cold or other upper respiratory or pharyngeal infection comprising administering to a subject the oral rinse or mouthwash of embodiment 55.

58. The method of embodiments 56 or 57, wherein the step of administering comprises spraying the aerosol into the mouth and/or pharynx of the subject.

Having described preferred embodiments of the invention, it is to be understood that the invention is not limited to the precise embodiments, and that various changes and modifications may be effected therein by those skilled in the art without departing from the scope or spirit of the invention as defined in the appended claims.

What is claimed is:

1. A composition formulated as a dentifrice gel or paste for inhibiting or reducing the incidence or likelihood of colds or other upper respiratory and pharyngeal infections, comprising
    (1) zinc gluconate, wherein the zinc gluconate ranges from 0.1% to 0.5% by weight of the composition; and
    (2) a tannin component, wherein the tannin component is 0.01% to 10% by weight of the composition; where the tannin component consists of a purified extract of gallic tannins that do not stain tooth enamel.

2. The composition of claim 1, further comprising a fluoride compound.

3. The composition of claim 1, wherein the composition is stored in a malleable or squeezable tube.

4. A composition formulated as chewing gum, oral rinse, mouth wash, or aerosol for inhibiting or reducing the incidence or likelihood of colds or other upper respiratory and pharyngeal infections, comprising a solvent or other vehicle comprising:
    (1) zinc gluconate, wherein the zinc gluconate ranges from 0.1% to 0.5% by weight of the composition; and
    (2) a tannin component, wherein the tannin component is 0.01% to 10% by weight of the composition; where the tannin component consists of a purified extract of gallic tannins that do not stain tooth enamel.

5. The composition of claim 4, further comprising a fluoride compound.

* * * * *